United States Patent
Burdine

(10) Patent No.: US 11,640,618 B1
(45) Date of Patent: May 2, 2023

(54) METHOD, APPARATUS, AND COMPUTER PROGRAM PRODUCT FOR PARTITIONING PRESCRIPTION TRANSACTION COSTS IN AN ELECTRONIC PRESCRIPTION TRANSACTION

(71) Applicant: McKesson Corporation, Irving, TX (US)

(72) Inventor: Jared Burdine, Dunwoody, GA (US)

(73) Assignee: MCKESSON CORPORATION, Irving, TX (US)

( * ) Notice: Subject to any disclaimer, the term of this patent is extended or adjusted under 35 U.S.C. 154(b) by 461 days.

(21) Appl. No.: 16/797,277

(22) Filed: Feb. 21, 2020

(51) Int. Cl.
| | |
|---|---|
| *G06Q 30/00* | (2012.01) |
| *G06Q 30/0201* | (2023.01) |
| *G16H 50/70* | (2018.01) |
| *G16H 20/00* | (2018.01) |
| *G06Q 30/0207* | (2023.01) |
| *G06Q 10/10* | (2023.01) |

(52) U.S. Cl.
CPC ........ *G06Q 30/0206* (2013.01); *G06Q 10/10* (2013.01); *G06Q 30/0213* (2013.01); *G16H 20/00* (2018.01); *G16H 50/70* (2018.01)

(58) Field of Classification Search
CPC .. G06Q 30/0206; G06Q 10/10; G06Q 30/213; G06Q 30/0213
See application file for complete search history.

(56) References Cited

U.S. PATENT DOCUMENTS

| | | | | |
|---|---|---|---|---|
| 7,912,741 | B1* | 3/2011 | Pinsonneault | G06Q 40/08 600/300 |
| 8,639,523 | B1* | 1/2014 | Pinsonneault | G16H 20/10 705/2 |
| 11,170,394 | B1* | 11/2021 | Macinski | G16H 20/10 |
| 2007/0276697 | A1* | 11/2007 | Wiley | G06Q 30/0207 705/2 |
| 2012/0109839 | A1* | 5/2012 | Anderson | G06Q 10/1057 705/322 |
| 2014/0214435 | A1* | 7/2014 | Previdi | G06Q 40/08 705/2 |

(Continued)

OTHER PUBLICATIONS

Davies, R., Specialty drugs: Four options for managing costs: With specialty drug costs growing at a double-digit pace and new drugs entering the market, plan sponsors struggle to keep up. the author describes challenges plan sponsors face with some particular . . . , 2017, Benefits Magazine (Year: 2017).*

*Primary Examiner* — Matthew L Hamilton
(74) *Attorney, Agent, or Firm* — Alston & Bird LLP

(57) ABSTRACT

A method, apparatus and computer program product are provided for partitioning prescription transaction costs by determining offset savings amounts to be applied to prescription transactions, based on an adjudicated response from a payer computer. Prescription transactions received from a pharmacy are submitted in real time or near real-time for adjudication. Historical data associated with the patient and prescription is accessed to identify a target patient pay amount. Based on the benefit coverage and/or co-pay amount from the adjudicated response, an offset savings is determined in real-time or near real-time that will partition the prescription transaction cost such that the remaining patient pay amount is aligned with the target patient pay amount.

15 Claims, 2 Drawing Sheets

(56) References Cited

U.S. PATENT DOCUMENTS

2015/0234991 A1\* 8/2015 Pinsonneault ......... G06Q 40/08
            705/3
2015/0278472 A1\* 10/2015 King ...................... G16H 20/10
            705/2
2016/0358293 A1\* 12/2016 Berger ............... G06Q 30/0207
2017/0255759 A1\* 9/2017 McGrath ................ G16H 20/10
2021/0374872 A1\* 12/2021 Stewart .................. G16H 50/20

\* cited by examiner

METHOD, APPARATUS, AND COMPUTER PROGRAM PRODUCT FOR PARTITIONING PRESCRIPTION TRANSACTION COSTS IN AN ELECTRONIC PRESCRIPTION TRANSACTION

TECHNOLOGICAL FIELD

Embodiments of the present invention relate generally to prescription transactions and, more particularly, to methods, apparatuses, and computer program products for partitioning prescription transaction costs by determining offset savings amounts to be applied to electronic prescription transactions, based on an adjudicated response, such as from a payer computer.

BACKGROUND

The ever changing and complex system relating to prescription drug pricing, and insurance coverage thereof often leads to surprise for customers when obtaining a prescription from a pharmacy. Some customers may experience a price shock when visiting a pharmacy or inquiring with a pharmacy to obtain a prescription due to lack of knowledge regarding the cost of such a prescription.

In some instances, a customer who obtains the same prescription on a routine basis may even experience changes in out-of-pocket cost due to a variety of factors, such as but not limited to price changes of the prescription by the drug manufacturer, varying rebate amounts or co-pay assistance provided by the drug manufacturer, fluctuations in the insurance provider's contract pricing, and/or the like. Additionally, once a patient meets their deductible set by an insurance plan, the out-of-pocket cost or co-pay for the same prescription may change. Fluctuations in pricing may in some cases lead to medication adherence issues, such as when a patient is prescribed a prescription, but fails to take the prescription due to the unexpected price of the prescription when visiting the pharmacy. Failure to adhere to the prescribed plan of care may not only risk the patient's health, but also impact profitability of drug manufacturers, pharmacies, and/or the like.

BRIEF SUMMARY

Methods, apparatuses, and computer program products are therefore provided for partitioning costs of prescription transactions by determining offset savings amounts to be applied to prescription transactions, based on an adjudicated response from a payer computer, thereby providing improved consistency in prescription pricing for a patient.

An apparatus is provided, comprising at least one processor and at least one memory including computer program code, the at least one memory and the computer program code configured to, with the processor, cause the apparatus to at least receive, from a pharmacy computer, an indication of a prescription transaction comprising a patient identifier identifying a patient and a prescription identifier identifying a drug. The at least one memory and computer program code may be further configured to access historical data relating to at least one prior patient copay associated with the patient identifier and the prescription identifier to determine a target patient pay amount, and transmit a prescription claim associated with the prescription transaction to a payer computer.

The at least one memory and computer program code may be further configured to receive an adjudicated prescription claim transaction associated with the prescription transaction, the adjudicated prescription claim transaction comprising a co-pay amount. The at least one memory and computer program code may be further configured to determine an offset savings amount to be applied to the adjudicated prescription claim transaction such that a remaining patient pay amount is within a threshold range of the target patient pay amount, and provide the remaining patient pay amount to the pharmacy computer.

According to certain embodiments, the adjudicated prescription claim transaction comprising the patient co-pay amount is provided based on at least a determination of whether a deductible has been met. The at least one memory and the computer program code are further configured to, with the processor, cause the apparatus to at least confirm the determined offset savings amount adheres to a contract with a third party specifying a maximum offset savings amount the third party will pay, and provide the offset savings amount to the third party, such as but not limited to a drug manufacturer.

According to certain embodiments, the target patient pay amount equals a last paid amount by the patient for the drug. The remaining patient pay amount may be provided to the pharmacy computer in real-time or near real-time responsive to receiving the indication of the prescription transaction from the pharmacy computer.

A method is provided, receiving, from a pharmacy computer, an indication of a prescription transaction comprising a patient identifier identifying a patient and a prescription identifier identifying a drug, and accessing historical data relating to at least one prior patient copay associated with the patient identifier and the prescription identifier to determine a target patient pay amount.

The method may include transmitting a prescription claim associated with the prescription transaction to a payer computer, and receiving an adjudicated prescription claim transaction associated with the prescription transaction, the adjudicated prescription claim transaction comprising a co-pay amount. The method may further include determining an offset savings amount to be applied to the adjudicated prescription claim transaction such that a remaining patient pay amount is within a threshold range of the target patient pay amount, and providing the remaining patient pay amount to the pharmacy computer.

The adjudicated prescription claim transaction may comprise the patient co-pay amount is provided based on at least a determination of whether a deductible has been met. The method may further include confirming the determined offset savings amount adheres to a contract with a third party specifying a maximum offset savings amount the third party will pay, and providing the offset savings amount to the third party, such a but not limited to a drug manufacturer. The remaining patient pay amount may be provided to the pharmacy computer in real-time or near real-time responsive to receiving the indication of the prescription transaction from the pharmacy computer.

A computer program product is provided, comprising at least one non-transitory computer-readable storage medium having computer-executable program code instructions stored therein, the computer-executable program code instructions comprising program code instructions to receive, from a pharmacy computer, an indication of a prescription transaction comprising a patient identifier identifying a patient and a prescription identifier identifying a drug. The computer-executable program code instructions may include program code instructions to access historical data relating to at least one prior patient copay associated with the patient identifier and the prescription identifier to determine a target patient pay amount, and transmit a prescription claim associated with the prescription transaction to a payer computer.

The computer-executable program code instructions may include program code instructions to receive an adjudicated prescription claim transaction associated with the prescription transaction, the adjudicated prescription claim transaction comprising a co-pay amount. The computer-executable program code instructions may include program code instructions to determine an offset savings amount to be applied to the adjudicated prescription claim transaction such that a remaining patient pay amount is within a threshold range of the target patient pay amount, and provide the remaining patient pay amount to the pharmacy computer.

In certain embodiments, the adjudicated prescription claim transaction comprising the patient co-pay amount is provided based on at least a determination of whether a deductible has been met. The computer-executable program code instructions may include program code instructions to confirm the determined offset savings amount adheres to a contract with a third party specifying a maximum offset savings amount the third party will pay, and provide the offset savings amount to the third party, such as but not limited to a drug manufacturer. According to certain embodiments, the target patient pay amount equals a last paid amount by the patient for the drug.

According to certain embodiments, the remaining patient pay amount is provided to the pharmacy computer in real-time or near real-time responsive to receiving the indication of the prescription transaction from the pharmacy computer.

An apparatus is provided with means for receiving, from a pharmacy computer, an indication of a prescription transaction comprising a patient identifier identifying a patient and a prescription identifier identifying a drug, and accessing historical data relating to at least one prior patient copay associated with the patient identifier and the prescription identifier to determine a target patient pay amount.

The apparatus may include means for transmitting a prescription claim associated with the prescription transaction to a payer computer, and means for receiving an adjudicated prescription claim transaction associated with the prescription transaction, the adjudicated prescription claim transaction comprising a co-pay amount. The method may further include means for determining an offset savings amount to be applied to the adjudicated prescription claim transaction such that a remaining patient pay amount is within a threshold range of the target patient pay amount, and means for providing the remaining patient pay amount to the pharmacy computer.

The above summary is provided merely for purposes of summarizing some example embodiments of the invention so as to provide a basic understanding of some aspects of the invention. Accordingly, it will be appreciated that the above described example embodiments are merely examples and should not be construed to narrow the scope or spirit of the disclosure in any way. It will be appreciated that the scope of the disclosure encompasses many potential embodiments, some of which will be further described below, in addition to those here summarized.

BRIEF DESCRIPTION OF THE SEVERAL VIEWS OF THE DRAWINGS

Figure 1:
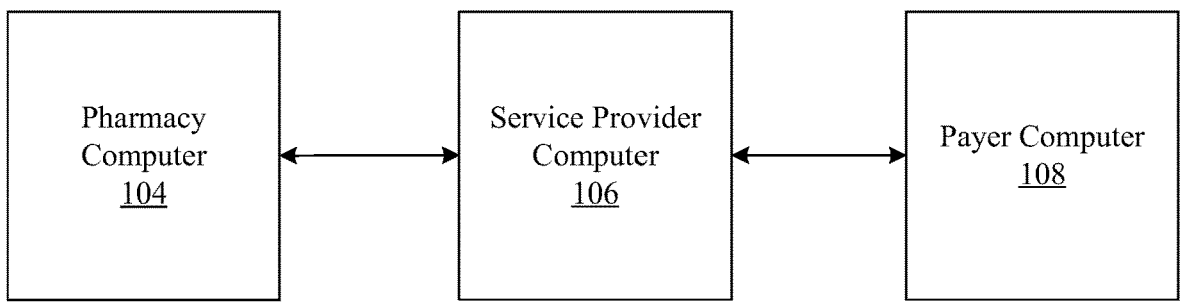
Figure 2:
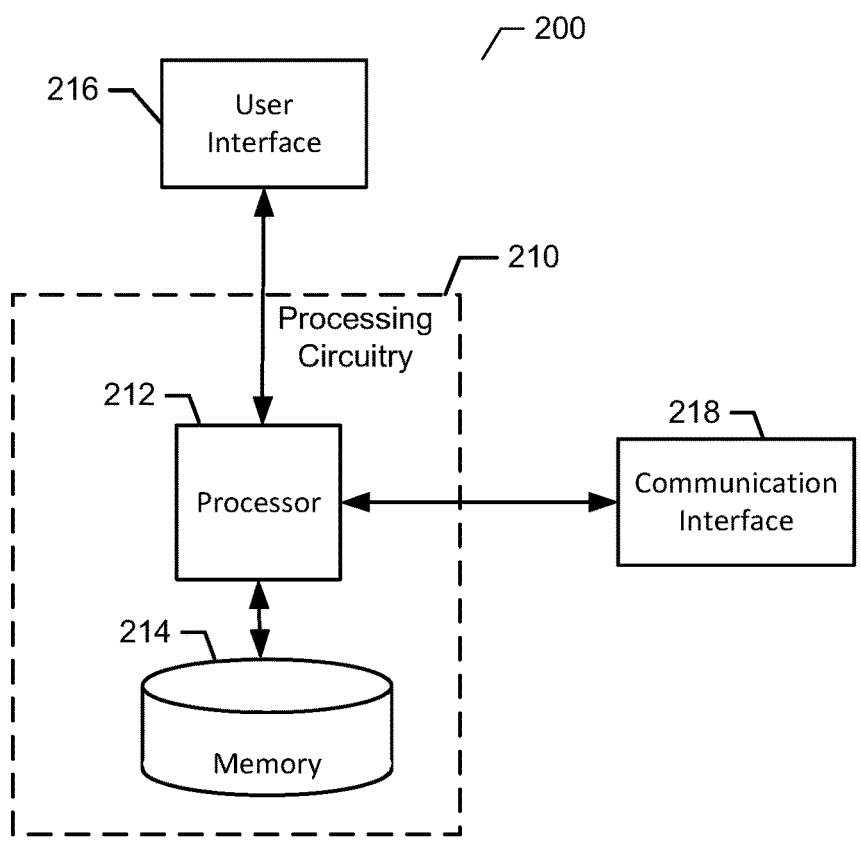
Figure 3:
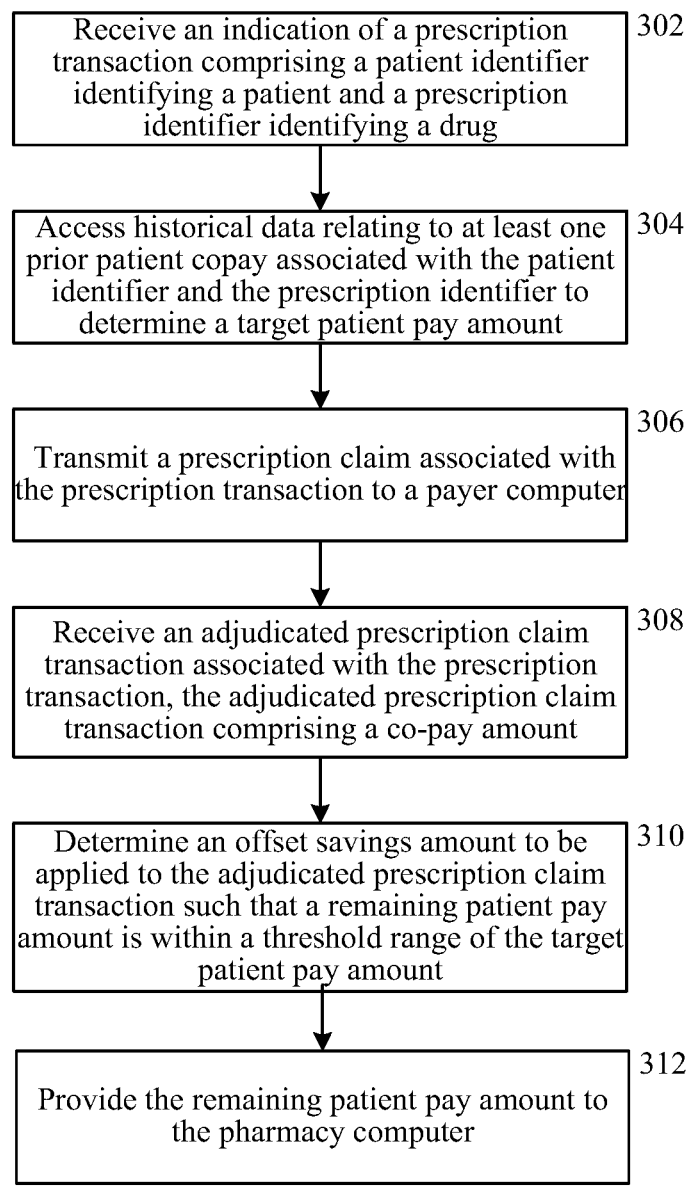

Having thus described embodiments of the invention in general terms, reference will now be made to the accompanying drawings, which are not necessarily drawn to scale, and wherein:

FIG. 1 is an example overview of a system that can be used to practice some example embodiments described herein;

FIG. 2 is an exemplary schematic diagram of an apparatus in accordance with some example embodiments; and FIG. 3 is a flowchart of operations that may be performed in accordance with some example embodiments.

DETAILED DESCRIPTION

Some embodiments of the present invention will now be described more fully hereinafter with reference to the accompanying drawings, in which some, but not all embodiments of the invention are shown. Indeed, various embodiments of the invention may be embodied in many different forms and should not be construed as limited to the embodiments set forth herein; rather, these embodiments are provided so that this disclosure will satisfy applicable legal requirements. Like reference numerals refer to like elements throughout.

As used herein, where a computing device is described to receive data from another computing device, it will be appreciated that the data may be received directly from the other computing device and/or may be received indirectly via one or more intermediary computing devices, such as, for example, one or more servers, relays, routers, network access points, and/or the like. Similarly, where a computing device is described herein to transmit data to other computing device, it will be appreciated that the data may be sent directly to the other computing device or may be sent to the other computing device via one or more interlinking computing devices, such as, for example, one or more servers, relays, routers, network access points, and/or the like.

FIG. 1 is an overview of a system that can be used to partition prescription transaction costs by determining offset savings amounts to be applied to prescription transactions, based on an adjudicated response from a payer computer according to certain example embodiments described herein. The pharmacy computer 104 may be associated with a pharmacy or pharmacy network to facilitate the filling of prescriptions, transmitting health insurance claims to a service provider computer 106, and/or the like. The pharmacy computer 104 may additionally or alternatively be associated with a physician's office, clinic, long-term care facility, hospital, etc. Accordingly, while the exemplary pharmacy computer 104 may be frequently referenced herein as part of a pharmacy or pharmacy network, the pharmacy computer 104 may be associated with any other healthcare provider, such as a physician's office, hospital and/or other medical facility.

The pharmacy computer 104 may be any processor-driven device that facilitates the submission of prescription transaction requests made by patients or consumers and the communication of information associated with prescription transactions to the service provider computer 106. In certain example embodiments, the pharmacy computer 104 may be a point of sale device associated with a pharmacy. The execution of the computer-implemented instructions by the pharmacy computer 104 may form a special purpose computer or other particular machine that is operable to facilitate the submission of pharmacy transaction requests made by patients, pharmacists, and/or the like, and the communication of information associated therewith to a service provider computer 106.

The service provider computer 106 may include, but is not limited to, a processor-driven device that is configured for receiving, processing, and fulfilling prescription requests from the pharmacy computer 104 and/or the payer computer 108 (described below), relating to prescription tracking, claims processing, benefits, billing, other healthcare transactions, and/or other related activities. Additionally or alternatively, the service provider computer 106 may be operable to facilitate the receipt, routing, and/or processing of healthcare transactions such as prescription transactions and/or associated responses amongst various components and/or subsystems such as, but not limited to, those depicted in FIG. 1.

In certain exemplary embodiments, the service provider computer 106 may be configured as or may comprise a switch or router that evaluates, modifies, reformats, generates, and/or routes healthcare transactions such as prescription transactions. For example, the service provider computer 106 may route prescription transactions communicated from the pharmacy computer 104 to a payer computer 108, such as that associated with a pharmacy benefits manager (PBM), an insurer, a Medicare or other government healthcare insurance program payer, or other payer. According to certain embodiments, the payer computer 108 may comprise any other computer system that receives and adjudicates a prescription transaction on behalf of the payer.

Additionally or alternatively, the service provider computer 106 may reformat healthcare transactions into another form of transaction and modify the recipient information of the reformatted transaction before routing the reformatted transaction to another party, such as a payer computer 108. The service provider computer 106 may also optionally apply edits to at least some of the healthcare transactions.

The service provider computer 106 may transmit responses from the payer computer regarding the prescription transaction to the pharmacy computer 104. For example, the service provider computer 106 may notify the pharmacy computer 104 of a co-pay or out-of-pocket costs to be paid by the patient for the prescription and/or the benefit applied to the prescription transaction. In this regard, a message or other notification may be appended to or included in the response transmitted to the pharmacy computer 104. Any of the aforementioned responses may be provided to the pharmacy computer 104 together with the prescription transaction response, or the service provider computer 106 may reformat the prescription transaction to include the details of such responses, and transmit the reformatted healthcare transaction back to the pharmacy computer 104.

Referring now to FIG. 2, apparatus 200 is a computing device(s) configured for implementing pharmacy computer 104, service provider computer 106, and/or payer computer 108, according to example embodiments.

Apparatus 200 may at least partially or wholly embody or be embodied by any of the pharmacy computer 104, service provider computer 106, and/or payer computer 108. Apparatus 200 may therefore implement any of the pharmacy computer 104, service provider computer 106, and/or payer computer 108, in accordance with some example embodiments, or may be implemented as a distributed system that includes any of the pharmacy computer 104, service provider computer 106, payer computer 108, and/or associated network(s).

It should be noted that the components, devices, and elements illustrated in and described with respect to FIG. 2 may not be mandatory and thus some may be omitted in certain embodiments. For example, FIG. 2 illustrates a user interface 216, as described in more detail below, which may be optional in any of the pharmacy computer 104 (such as when the pharmacy computer 104 is implemented as a service communicatively connected to a work station or other user device utilized by a pharmacist or other pharmacy employee), service provider computer 106, and/or payer computer 108. Additionally, some embodiments may include further or different components, devices, or elements beyond those illustrated in and described with respect to FIG. 2.

Continuing with FIG. 2, processing circuitry 210 may be configured to perform actions in accordance with one or more example embodiments disclosed herein. In this regard, the processing circuitry 210 may be configured to perform and/or control performance of one or more functionalities of apparatus 200 in accordance with various example embodiments. The processing circuitry 210 may be configured to perform data processing, application execution, and/or other processing and management services according to one or more example embodiments. In some embodiments apparatus 200, or a portion(s) or component(s) thereof, such as the processing circuitry 210, may be embodied as or comprise a circuit chip. The circuit chip may constitute means for performing one or more operations for providing the functionalities described herein.

In some example embodiments, the processing circuitry 210 may include a processor 212, and in some embodiments, such as that illustrated in FIG. 2, may further include memory 214. The processing circuitry 210 may be in communication with or otherwise control a user interface 216, and/or a communication interface 218. As such, the processing circuitry 210, such as that included in any of the pharmacy computer 104, service provider computer 106, payer computer 108, and/or apparatus 200 may be embodied as a circuit chip (e.g., an integrated circuit chip) configured (e.g., with hardware, software, or a combination of hardware and software) to perform operations described herein.

The processor 212 may be embodied in a number of different ways. For example, the processor 212 may be embodied as various processing means such as one or more of a microprocessor or other processing element, a coprocessor, a controller, or various other computing or processing devices including integrated circuits such as, for example, an ASIC (application specific integrated circuit), an FPGA (field programmable gate array), or the like. Although illustrated as a single processor, it will be appreciated that the processor 212 may comprise a plurality of processors. The plurality of processors may be in operative communication with each other and may be collectively configured to perform one or more functionalities of apparatus 200 as described herein. The plurality of processors may be embodied on a single computing device or distributed across a plurality of computing devices collectively configured to function as pharmacy computer 104, service provider computer 106, payer computer 108, and/or apparatus 200. In some example embodiments, the processor 212 may be configured to execute instructions stored in the memory 214 or otherwise accessible to the processor 212. As such, whether configured by hardware or by a combination of hardware and software, the processor 212 may represent an entity (e.g., physically embodied in circuitry— in the form of processing circuitry 210) capable of performing operations according to embodiments of the present invention while configured accordingly. Thus, for example, when the processor 212 is embodied as an ASIC, FPGA, or the like, the processor 212 may be specifically configured hardware for conducting the operations described herein. Alternatively, as another example, when the processor 212 is embodied as an executor of software instructions, the instructions may specifically configure the processor 212 to perform one or more operations described herein.

In some example embodiments, the memory 214 may include one or more non-transitory memory devices such as, for example, volatile and/or non-volatile memory that may be either fixed or removable. In this regard, the memory 214 may comprise a non-transitory computer-readable storage medium. It will be appreciated that while the memory 214 is illustrated as a single memory, the memory 214 may comprise a plurality of memories. The plurality of memories may be embodied on a single computing device or may be distributed across a plurality of computing devices. The memory 214 may be configured to store information, data, applications, computer program code, instructions and/or the like for enabling apparatus 200 to carry out various functions in accordance with one or more example embodiments. For example, when apparatus 200 is implemented as service provider computer 106, memory 214 may be configured to store computer program code for performing corresponding functions thereof, as described herein according to example embodiments.

Still further, memory 214 may be configured to store routing tables, that facilitate determining the destination of communications received from a pharmacy computer 104, and/or payer computer 108. Memory 214 may further include reconciliation tables for tracking the healthcare transactions received from the pharmacy computer 104, and reconciling them with responses received from payer computer 108. The memory 214 may further comprise a database comprising historical prescription transaction information, provided by the pharmacy computer 104 and/or payer computer 108. For example, the memory 214 may store historical co-pay and/or out-of-pocket cost information of particular prescriptions paid for by particular patients under a healthcare insurance plan. The memory 214 may be modified as described herein, to reformat prescription transactions with additional information received, determined and/or generated according to example embodiments.

The memory 214 may be further configured to buffer input data for processing by the processor 212. Additionally or alternatively, the memory 214 may be configured to store instructions for execution by the processor 212. In some embodiments, the memory 214 may include one or more databases that may store a variety of files, contents, or data sets. Among the contents of the memory 214, applications may be stored for execution by the processor 212 to carry out the functionality associated with each respective application. In some cases, the memory 214 may be in communication with one or more of the processor 212, user interface 216, and/or communication interface 218, for passing information among components of apparatus 200.

The optional user interface 216 may be in communication with the processing circuitry 210 to receive an indication of a user input at the user interface 216 and/or to provide an audible, visual, mechanical, or other output to the user. As such, the user interface 216 may include, for example, a keyboard, a mouse, a display, a touch screen display, a microphone, a speaker, and/or other input/output mechanisms. As such, in embodiments in which apparatus 200 implemented as the pharmacy computer 104, the user interface 216 may, in some example embodiments, provide means for user entry of insurance information, details relating to the dispense of a prescription, and/or the like. The user interface 216 may be further configured to display or provide co-pay and/or out-of-pocket costs of prescriptions, such as when apparatus 200 is implemented as a pharmacy computer 104. In some example embodiments, aspects of user interface 216 may be limited or the user interface 216 may not be present.

The communication interface 218 may include one or more interface mechanisms for enabling communication with other devices and/or networks. In some cases, the communication interface 218 may be any means such as a device or circuitry embodied in either hardware, or a combination of hardware and software that is configured to receive and/or transmit data from/to a network and/or any other device or module in communication with the processing circuitry 210. By way of example, the communication interface 218 may be configured to enable communication amongst any of pharmacy computer 104, service provider computer 106, payer computer 108, and/or apparatus 200 over a network. Accordingly, the communication interface 218 may, for example, include supporting hardware and/or software for enabling wireless and/or wireline communications via cable, digital subscriber line (DSL), universal serial bus (USB), Ethernet, or other methods.

A network, such as the network in which any of the systems of FIG. 1 or components thereof or components described herein may operate, (e.g., provider computer 104, service provider computer 106, payer computer 108, apparatus 200, and/or the like) may include a local area network, the Internet, any other form of a network, or any combination thereof, including proprietary private and semi-private networks and public networks. The network may comprise a wired network and/or a wireless network (e.g., a cellular network, wireless local area network, wireless wide area network, some combination thereof, and/or the like).

Having now described an example apparatus for implementing example embodiments, FIG. 3 is a flowchart illustrating example operations of an apparatus 200, according to some example embodiments. The operations of FIG. 3 may be performed by apparatus 200, such as with the service provider computer 106, and/or the like.

As shown by operation 302, apparatus 200 may include means, such as processor 212, memory 214, communication interface 218, and/or the like, for receiving an indication of a prescription transaction comprising a patient identifier identifying a patient and a prescription identifier identifying a drug. The prescription transaction may be received from the pharmacy computer 104, such as following entry by a pharmacist or other user of data relating to a prescription drug being obtained by a patient. In this regard, the prescription transaction may include a prescription claim entered by a healthcare provider, such as a pharmacist, and may include one or more of the following information:

Payer ID/Routing Information
Transaction Payer Identifier(s) that designates a destination of the healthcare transaction (e.g., BIN Number, BIN Number and PCN, or BIN Number and Group ID)
Transaction Code
Patient Information
Name (e.g. Patient Last Name, Patient First Name, etc.)
Date of Birth of Patient
Age of Patient
Patient Gender Code
Patient Address (e.g. Street Address, Zip Code, etc.)
Patient Contact Information (e.g. patient telephone number, email address, etc.)
Patient Health Condition Information
Patient Identification Identifier (such as, but not limited to, patient social security number, a subset of the patient social security number, health insurance claim number (HICN), cardholder ID, etc.)

Insurance/Coverage Information
Cardholder Name (e.g. Cardholder First Name, Cardholder Last Name)
Cardholder ID and/or other identifier (e.g. person code)
Group ID and/or Group Information
Prescriber Information
Primary Care Provider ID or other identifier (e.g. NPI code)
Primary Care Provider Name (e.g. Last Name, First Name)
Prescriber ID or other identifier (e.g. NPI code, DEA number)
Prescriber Name (e.g. Last Name, First Name)
Prescriber Contact Information (e.g. Telephone Number)
Pharmacy or other Healthcare Provider Information (e.g. store name, chain identifier, etc.)
Pharmacy or other Healthcare Provider ID (e.g. NPI code)
Claim Information
Drug, service, or product information (e.g. via National Drug Code (NDC) number)
Prescription/Service Reference Number
Date Prescription Written
Quantity Dispensed
Days' Supply
Diagnosis/Condition
Pricing information for the drug/service/product
Number of Refills Authorized
One or more Drug Utilization (DUR) Codes
Date of Service
Intermediary Authorization Field The prescription transaction may be received at the service provider 106 for further processing as described below.

As shown by operation 304, apparatus 200 may include means, such as processor 212, memory 214, communication interface 218, and/or the like, for accessing historical data relating to at least one prior patient copay associated with the patient identifier and the prescription identifier to determine a target patient pay amount. The patient identifier received with the prescription transaction may be used to access the historical data stored by memory 214, such as a historical pricing database, for example. The historical data may include data previously provided by the pharmacy computer 104, or other source, indicating a previous amount paid out-of-pocket by the patient for the same prescription, identified by the prescription identifier. In this regard, the target patient pay amount may be determined as the last paid amount by the patient for the drug.

Example embodiments may access the historical data stored by memory 214 in real-time or near real-time responsive to the receipt of the prescription transaction, enabling a real-time or near real-time response to be provided to the pharmacy computer 104 as described in further detail below. As used throughout, the terms real-time and near real-time to indicate a seemingly instant response time at the pharmacy computer 104, such that a patient obtaining a prescription may obtain pricing information as the pharmacist or other employee interacts with a user interface of the pharmacy computer 104 or a user interface in communication with the pharmacy computer 104. It will be appreciated that despite the reference to real-time or near real-time, certain delays based on computer processing time may be encountered.

It will be appreciated that the historical data accessed from memory 214 may be used in other manners to determine a target patient pay amount. For example, in instances in which the historical data reflect varying pricing data for the same prescription drug obtained by the same patient, example embodiments may utilize an average out-of-pocket cost for the prescription paid by the patient. In this regard, the historical data may reflect amounts previously paid by a patient out-of-pocket for a particular prescription, regardless of insurance coverage, drug manufacturer rebates, and/or the like. Similarly, the target patient pay amount determined with regard to operation 304 may be an amount the patient expects to pay out-of-pocket for the prescription, regardless of insurance coverage, drug manufacturer rebates, and/or the like.

As another example, in a scenario in which no historical data is available for the prescription identifier and patient identifier, example embodiments may access historical data comprising out-of-pocket costs paid by other patients, and possibly patients having the same or similar healthcare insurance plan as the subject patient, to determine the target patient pay amount. In this regard, the target patient pay amount may be the amount that example embodiments, such as provided by service provider computer 106, aims to charge a patient for the prescription.

As shown by operation 306, apparatus 200 may include means, such as processor 212, memory 214, communication interface 218, and/or the like, for transmitting a prescription claim associated with the prescription transaction to a payer computer, such as payer computer 108. Example embodiments may access a routing table or other data to determine a recipient payer computer 108 to which to transmit a prescription claim. In this regard, example embodiments may generate the prescription claim from information provided in the prescription transaction, or forward the prescription transaction to the payer computer 108 accordingly. The prescription claim may be transmitted to the payer computer 108 in real-time or near real-time in response to receiving the prescription transaction from the pharmacy computer 104, thereby enabling the service provider 106 to provide a response to the pharmacy computer 104 regarding out-of-pocket costs, as described in further detail below, in real-time or near real-time.

Once received from the service provider computer 106, the payer computer 108 may process the prescription claim and generate a benefit response message. For example, the payer computer 108 may adjudicate the prescription claim, such as according to plan policies. The payer computer 108 may access prior claim details for the patient, and/or amounts previously paid by the patient to determine whether the deductible has been met. In this regard, the payer computer 108 may include in the benefit response message the benefit amount and/or remaining balance owed for the prescription identified in the prescription claim. Other rules and/or requirements may be processed and/or validated to determine the benefit response. The benefit response message may be appended to or incorporated with the prescription claim, such that when received by the service prover computer 106, the service provider computer 106 can identify the source of the response as associated with the originating prescription transaction received in operation 302. The processed, or adjudicated claim, may be transmitted back to the service provider computer 106 as an adjudicated prescription claim transaction. As set forth above, the adjudicated prescription claim transaction comprising the patient co-pay amount may be provided based on at least a determination of whether a deductible has been met Accordingly, in operation 308, apparatus 200 may include means, such as processor 212, memory 214, communication interface 218, and/or the like, to receive an adjudicated prescription claim transaction associated with the prescription transaction, the adjudicated prescription claim transaction comprising a co-pay amount. In this regard, the co-pay amount received in the adjudicated prescription claim transaction may be considered an initial co-pay provided by the payer computer 108, and may, according to certain embodiments, be further reduced as set forth below.

As shown by operation 310, apparatus 200 may include means, such as processor 212, memory 214, and/or the like, to determine an offset savings amount to be applied to the adjudicated prescription claim transaction such that a remaining patient pay amount is within a threshold range of the target patient pay amount. The offset savings amount may be considered an amount needed to credit the transaction and/or patient such that the out-of-pocket cost paid by the patient aligns with the target patient pay amount. Aligning the remaining out-of-pocket cost with the target patient pay amount may include determining the offset savings amount by which to reduce the co-pay such that the co-pay amount equals the target patient pay amount, or is within a predetermined or calculated threshold range of the target patient pay amount. For example, the offset savings amount may be determined such that the remaining patient pay amount is within 5% of the target patient pay amount. As another example, the offset savings amount may be determined such that the remaining patient pay amount is equal to the target patient pay amount.

For example, if the co-pay amount provided in operation 308 is higher than the target patient pay amount, example embodiments may calculate the difference between the co-pay and the target patient pay amount, as the offset savings amount.

According to certain embodiments, the offset savings amount may be paid for by a third party, such as the drug manufacturer. For example, some drug manufacturers may participate in an e-voucher program and/or co-pay assistance program to make their drugs more affordable for patients. In this regard, the third party, such as a drug manufacturer, may have a contractual agreement with a pharmacy associated with the pharmacy computer 104, and/or the service provider 106, regarding the offset savings that may be applied to a particular prescription drug. Contractual amounts may be stored in a database table, for example, indicating a maximum offset savings amount per patient to be applied each time the prescription is obtained.

As such, in certain embodiments, once the offset savings amount is determined by apparatus 200, apparatus 200 may be further configured, such as with processor 212, memory 214, and/or the like, to confirm the determined offset savings amount adheres to a contract with a third party specifying a maximum offset savings amount the third party will pay. In certain embodiments, apparatus 200, such as service provider 106, may transmit the offset savings amount to the third party so that the third party (e.g., drug manufacturer) pays the offset savings amount to the pharmacy.

In certain embodiments, a maximum amount allowed by the third party, such as a drug manufacturer, may exceed the amount needed to reduce the patient pay amount to the target patient pay amount. In such scenarios, example embodiments may determine the offset savings amount to be less than the maximum amount permitted to be paid by the third party (e.g., drug manufacturer). Such embodiments may save the third party money by systematically determining the target patient pay amount as an amount the patient is willing to pay for the drug, and may prevent discounting the prescription beyond what is necessary to have the patient complete the prescription transaction. In this regard, the benefit or co-pay assistance provided by the third party (e.g., drug manufacturer) may be reduced. In this regard, some costs savings may be returned to the third party (e.g., drug manufacturer), and repurposed for other means such as savings to other patients, savings for different prescription drugs, re-allocated funds for research and development, and/or the like.

As another example, the offset savings amount calculated by example embodiments, needed to reach the target patient pay amount, may be too high to be covered by the third party (e.g., drug manufacturer) according to a contractual agreement. In such examples, various solutions may be applied. In some embodiments, the service provider associated with the service provider computer 106 may apply an additional credit or savings to align the out-of-pocket cost with the target patient pay amount. As another example, the service provider computer 106 may present an option to the pharmacy computer 104 to cover any remaining difference from the offset savings needed to reach the target patient pay amount. In some embodiments, the offset savings amount may only be partially applied as permitted by the third party (e.g., drug manufacturer), such that the remaining patient pay amount does not exactly match the target patient pay amount, but may still be reduced relative to the co-pay amount provided by the payer computer 108, to provide an improved consistency in pricing for the patient. The improved consistency in prescription drug pricing may be reflected by reduced variance in prescription drug pricing for the patient, or reduced variance in prescription drug pricing for a group of patients, such as a group of patients in an insurance plan. A plot of prices of a prescription drug for a patient or group of patients may therefore be smoothed, such as by utilizing polynomial regression. According to certain embodiments, an abandonment profile may be determined, for a particular prescription drug or group of prescription drugs. The abandonment profile may be smoothed, such as by using polynomial regression.

In any event, as shown by operation 312, apparatus 200 may include means, such as processor 212, memory 214, communication interface 218, and/or the like, to provide the remaining patient pay amount to the pharmacy computer. The processor 212 may be configured to calculate the remaining patient pay amount by subtracting the offset savings amount from the co-pay amount provided by the payer computer 108, for example. The result may be an adjusted co-pay, or out-of-pocket cost to be transmitted to the pharmacy computer 104 for provision via a user interface, such that the patient pay amount can be communicated to the patient. As such, the patient may experience more consistent pricing of prescriptions, in comparison to pricing experienced without implementation of the examples embodiments described herein. In this regard, example embodiments partition prescription transaction costs by determining offset savings amounts to be applied to prescription transactions, based on an adjudicated response from a payer computer. The consistency of prescription pricing may therefore be improved by reducing or eliminating fluctuations in pricing of a prescription drug for the same patient.

Example embodiments provided herein therefore provide a solution to the technical problem of inconsistent pricing of electronic prescription transactions. Due to the network-based implementation of real-time prescription claims processing, and the real-time demand for pricing to be provided to the patient or customer in the pharmacy while obtaining the prescription, a technical challenge is provided with regard to implementing consistent pricing, due to many factors outside of the control of the service provider tasked with acting as the intermediary between the pharmacy and payer. For instance, as set forth above, the service provider may not have access to information indicating whether an insurance plan deductible has been met.

In this regard, a technical solution as described above is provided to determine an offset savings amount based on the adjudication of a prescription claim transaction received from the payer computer 108. Example embodiments determine the offset savings amount in real-time responsive to the adjudicated prescription claims transaction, and therefore may provide a response to the pharmacy, in real-time or near real-time relative to the request made by the pharmacy, to provide consistent pricing of prescription drugs to a patient.

Accordingly, example embodiments provide improved medication adherence, by reducing sticker shock to patients and therefore reducing or eliminating circumstances in which the patient decides not to purchase a prescription due to the cost presented when initiating the prescription transaction from the pharmacy. Additionally, example embodiments may conserve or reduce processing resources and memory resources otherwise utilized by the pharmacy computer 104, service provider computer 106, and/or payer computer 108, to submit, process, and route coordination of benefits claims. For example, a reduction in copay may reduce instances in which a prescription expense or transaction is routed to two or more payers, thereby conserving a variety of system resources. Similarly, example embodiments may conserve or reduce processing resources and memory resources otherwise utilized by the pharmacy computer 104, service provider computer 106, and/or payer computer 108, to submit, process, and route prescription claim reversals, such as in instances in which the patient decides not to follow through with a prescription transaction due to the higher than expected out-of-pocket costs. These situations in which the resources expended to determine the out-of-pocket costs are wasted may be reduced by reducing the out-of-pocket costs in accordance with an example embodiment and correspondingly increasing the likelihood that a patient fills a prescription, thereby increasing the percentage of instances in which the expenditure of resources to determine the out-of-pocket costs is useful and worthwhile and results in patient adherence with the prescription.

It will be appreciated that the figures are each provided as examples and should not be construed to narrow the scope or spirit of the disclosure in any way. In this regard, the scope of the disclosure encompasses many potential embodiments in addition to those illustrated and described herein. Numerous other configurations may also be used to implement embodiments of the present invention.

FIG. 3 illustrates operations of a method, apparatus, and computer program product according to some example embodiments. It will be understood that each operation of the flowchart or diagrams, and combinations of operations in the flowchart or diagrams, may be implemented by various means, such as hardware and/or a computer program product comprising one or more computer-readable mediums having computer readable program instructions stored thereon. For example, one or more of the procedures described herein may be embodied by computer program instructions of a computer program product. In this regard, the computer program product(s) which embody the procedures described herein may comprise one or more memory devices of a computing device (for example, memory 214) storing instructions executable by a processor in the computing device (for example, by processor 212). In some example embodiments, the computer program instructions of the computer program product(s) which embody the procedures described above may be stored by memory devices of a plurality of computing devices. As will be appreciated, any such computer program product may be loaded onto a computer or other programmable apparatus (for example, apparatus 200) to produce a machine, such that the computer program product including the instructions which execute on the computer or other programmable apparatus creates means for implementing the functions specified in the flowchart block(s). Further, the computer program product may comprise one or more computer-readable memories on which the computer program instructions may be stored such that the one or more computer-readable memories can direct a computer or other programmable apparatus to function in a particular manner, such that the computer program product may comprise an article of manufacture which implements the function specified in the flowchart block(s). The computer program instructions of one or more computer program products may also be loaded onto a computer or other programmable apparatus (for example, apparatus 200 and/or other apparatus) to cause a series of operations to be performed on the computer or other programmable apparatus to produce a computer-implemented process such that the instructions which execute on the computer or other programmable apparatus implement the functions specified in the flowchart block(s).

Accordingly, blocks of the flowchart support combinations of means for performing the specified functions and combinations of operations for performing the specified functions. It will also be understood that one or more blocks of the flowchart, and combinations of blocks in the flowchart, can be implemented by special purpose hardware-based computer systems which perform the specified functions, or combinations of special purpose hardware and computer instructions.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. An apparatus comprising:
at least one processor and at least one memory including computer program code, the at least one memory and the computer program code configured to, with the processor, cause the apparatus to at least:
receive, from a pharmacy computer, an indication of a prescription transaction comprising a patient identifier identifying a patient and a prescription identifier identifying a drug; and in real-time or near real-time responsive to receiving the indication of the prescription transaction from the pharmacy computer:
    access historical data comprising at least one prior patient copay associated with the patient identifier and the prescription identifier;
    cause transmission of a prescription claim associated with the prescription transaction to a payer computer;
    receive an adjudicated prescription claim transaction associated with the prescription transaction, the adjudicated prescription claim transaction comprising a copay amount;
    calculate an offset savings amount to be applied to the adjudicated prescription claim transaction such that a remaining patient pay amount is within a threshold range of the at least one prior patient copay from the historical data, and the remaining patient pay amount is more consistent with the prior patient copay than if the offset savings amount were not applied, wherein calculating the offset savings amount comprises using at least one of polynomial regression or an average that incorporates the at least one prior patient copay from the historical data associated with the patient identifier and the prescription identifier; and
    cause transmission of the remaining patient pay amount to the pharmacy computer.

2. The apparatus according to claim 1, wherein the adjudicated prescription claim transaction comprising a patient copay amount is provided based on at least a determination of whether a deductible has been met.

3. The apparatus according to claim 1, wherein the at least one memory and the computer program code are further configured to, with the processor, cause the apparatus to at least:
    confirm the offset savings amount adheres to a contract with a third party specifying a maximum offset savings amount the third party will pay; and
    provide the offset savings amount to the third party.

4. The apparatus according to claim 3, wherein the third party is a drug manufacturer.

5. The apparatus according to claim 1, wherein the at least one prior patient copay equals a last paid amount by the patient for the drug.

6. A method comprising:
    receiving via a network, by a server, and from a pharmacy computer, an indication of a prescription transaction comprising a patient identifier identifying a patient and a prescription identifier identifying a drug; and
    in real-time or near real-time responsive to receiving the indication of the prescription transaction from the pharmacy computer:
        accessing, by the server, historical data comprising at least one prior patient copay associated with the patient identifier and the prescription identifier;
        causing transmission of a prescription claim associated with the prescription transaction to a payer computer;
        receiving an adjudicated prescription claim transaction associated with the prescription transaction, the adjudicated prescription claim transaction comprising a copay amount;
        calculating an offset savings amount to be applied to the adjudicated prescription claim transaction such that a remaining patient pay amount is within a threshold range of the at least one prior patient copay associated with the patient identifier and the prescription identifier, and the remaining patient pay amount is more consistent with the prior patient copay than if the offset savings amount were not applied, wherein calculating the offset savings amount comprises the server using at least one of polynomial regression or an average that incorporates the at least one prior patient copay from the historical data associated with the patient identifier and the prescription identifier; and
        causing transmission of the remaining patient pay amount to the pharmacy computer.

7. The method according to claim 6, wherein the adjudicated prescription claim transaction comprising a patient copay amount is provided based on at least a determination of whether a deductible has been met.

8. The method according to claim 6, further comprising:
    confirming the offset savings amount adheres to a contract with a third party specifying a maximum offset savings amount the third party will pay; and
    providing the offset savings amount to the third party.

9. The method according to claim 8, wherein the third party is a drug manufacturer.

10. The method according to claim 6, wherein the at least one prior patient copay equals a last paid amount by the patient for the drug.

11. A computer program product comprising at least one non-transitory computer-readable storage medium having computer-executable program code instructions stored therein, the computer-executable program code instructions comprising program code instructions to:
    receive, from a pharmacy computer, an indication of a prescription transaction comprising a patient identifier identifying a patient and a prescription identifier identifying a drug; and
    in real-time or near real-time responsive to receiving the indication of the prescription transaction from the pharmacy computer:
        access historical data comprising at least one prior patient copay associated with the patient identifier and the prescription identifier;
        cause transmission of a prescription claim associated with the prescription transaction to a payer computer;
        receive an adjudicated prescription claim transaction associated with the prescription transaction, the adjudicated prescription comprising a copay amount;
        calculate an offset savings amount to be applied to the adjudicated prescription claim transaction such that a remaining patient pay amount is within a threshold range of the at least one prior patient copay associated with the patient identifier and the prescription identifier, and the remaining patient pay amount is more consistent with the prior patient copay than if the offset savings amount were not applied, wherein calculating the offset savings amount comprises using at least one of polynomial regression or an average that incorporates the at least one prior patient copay from the historical data associated with the patient identifier and the prescription identifier; and
        cause transmission of the remaining patient pay amount to the pharmacy computer.

12. The computer program product according to claim 11, wherein the adjudicated prescription claim transaction comprising a patient copay amount is provided based on at least a determination of whether a deductible has been met.

13. The computer program product according to claim 11, wherein the computer-executable program code instructions further comprise program code instructions to:
   confirm the offset savings amount adheres to a contract with a third party specifying a maximum offset savings amount the third party will pay; and
   provide the offset savings amount to the third party.

14. The computer program product according to claim 13, wherein the third party is a drug manufacturer.

15. The computer program product according to claim 11, wherein the at least one prior patient copay equals a last paid amount by the patient for the drug.

\* \* \* \* \*